United States Patent [19]
Grabover et al.

[11] Patent Number: 5,876,330
[45] Date of Patent: Mar. 2, 1999

[54] ENDOSCOPE WITH SEMI-RIGID SHAFT AND MALLEABLE TIP AND METHOD OF MANUFACTURE

[75] Inventors: Edward A. Grabover, Danbury; Gregory S. Konstorum, Stamford, both of Conn.; Demetrius H. Bagley, Philadelphia, Pa.

[73] Assignee: Circon Corporation, Goleta, Calif.

[21] Appl. No.: 949,740

[22] Filed: Oct. 14, 1997

[51] Int. Cl.⁶ ...................................................... A61B 1/22
[52] U.S. Cl. ............................................ 600/129; 600/920
[58] Field of Search ...................................... 600/127, 129, 600/139, 140, 143, 920

[56] References Cited

U.S. PATENT DOCUMENTS

| | | | |
|---|---|---|---|
| 1,995,196 | 3/1935 | Wolf | 600/139 |
| 5,083,549 | 1/1992 | Cho et al. | 600/129 X |
| 5,199,417 | 4/1993 | Muller et al. | |
| 5,279,280 | 1/1994 | Bacich et al. | 600/140 X |
| 5,329,940 | 7/1994 | Adair | |
| 5,607,386 | 3/1997 | Flam | 600/120 |

*Primary Examiner*—Jeffrey A. Smith
*Attorney, Agent, or Firm*—Perman & Green, LLP

[57] ABSTRACT

An endoscope having a shaft with a semi-rigid tube and a malleable tube. The malleable tube is connected to and extends from a distal end of the semi-rigid tube. The connection of the two tubes includes dimples stamped into the semi-rigid tube that inwardly project into holes in the malleable tube.

20 Claims, 2 Drawing Sheets

5,876,330

ENDOSCOPE WITH SEMI-RIGID SHAFT AND MALLEABLE TIP AND METHOD OF MANUFACTURE

BACKGROUND OF THE INVENTION

1. Field Of The Invention

The present invention relates to endoscopes and, more particularly, to an endoscope with a malleable tip.

2. Prior Art

U.S. Pat. No. 5,329,940 discloses an endotracheal tube intubation assist device with a malleable elongated insertion section. U.S. pat. No. 5,199,417 discloses an endoscope with a semi-rigid proximal section and a deflectable distal section.

SUMMARY OF THE INVENTION

In accordance with one embodiment of the present invention an endoscope is provided having an elongate shaft. The shaft comprises a first section and a second section. The first section extends along a majority of the length of the shaft. The first section has a semi-rigid tube. The second section is connected to a distal end of the first section. The second section has a malleable tube which is adapted to be formed to a desired shape by hand. The first section provides the shaft with sufficient rigidity to access a target area through an aperture in a patient that exerts force on the shaft, and the second section can be pre-formed before insertion of the shaft into the patient to have the desired shape when a distal end of the shaft reaches the target area.

In accordance with another embodiment of the present invention, an endoscope is provided having an elongate shaft. The shaft comprises a first semi-rigid tube, and a second tube. The first tube is connected to a distal end of the first tube. The second tube is comprised of a hand malleable material. At least one of the tubes has holes and the other tube has sections that project into the holes to attach the two tubes together.

In accordance with one method of the present invention a method of manufacturing an endoscope shaft is provided comprising steps of providing a hand malleable tube with holes at a proximal end; positioning a semi-rigid tube on the proximal end of the hand malleable tube over the holes; and deforming the semi-rigid tube to form sections that project into the holes of the hand malleable tube and thereby attach the two tubes to each other.

BRIEF DESCRIPTION OF THE DRAWINGS

The foregoing aspects and other features of the invention are explained in the following description, taken in connection with the accompanying drawings, wherein.

DETAILED DESCRIPTION OF THE PREFERRED EMBODIMENT

Figure 1:
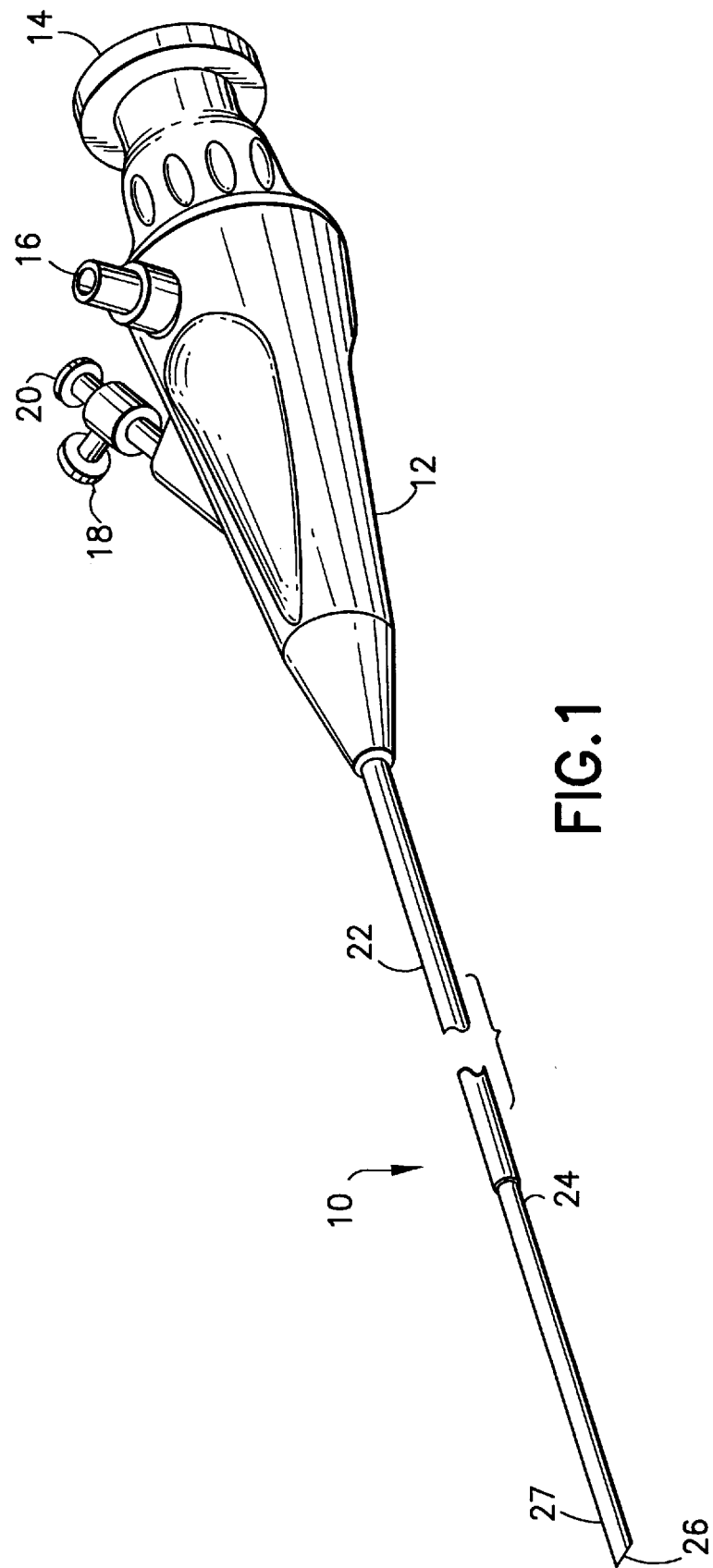
FIG. 1 is a perspective view of an endoscope incorporating features of the present invention.

Referring to FIG. 1, there is shown a perspective view of an endoscope 10 incorporating features of the present invention. Although the present invention will be described with reference to the single embodiment shown in the drawings, it should be understood that the present invention can be embodied in various different types and kinds of alternate embodiments. In addition, any suitable size, shape or type of elements or materials could be used.

The endoscope 10 generally comprises a proximal end having a housing 12, an eyepiece 14, a light post 16, a working channel through port 20, and an irrigation port 18. A similar endoscope proximal end is described in U.S. Pat. No. 5,199,417 which is hereby incorporated by reference in its entirety. In alternate embodiments, other types of proximal ends could be provided. In addition, the present invention could be used in other different types of endoscopes. Extending from the front of the housing 12 is an elongate shaft 22. The shaft 22 comprises a frame 24. Located inside the frame are working channels and fiber optics (not shown). The working channels provide a path from the ports 18, 20 to the distal tip 26 of the shaft 22. The fiber optics transmit light from a light source (not shown), connected to the light post 16, to the distal tip 26, and transmit an image from the distal tip 26 back to the eyepiece 14.

Figure 2:
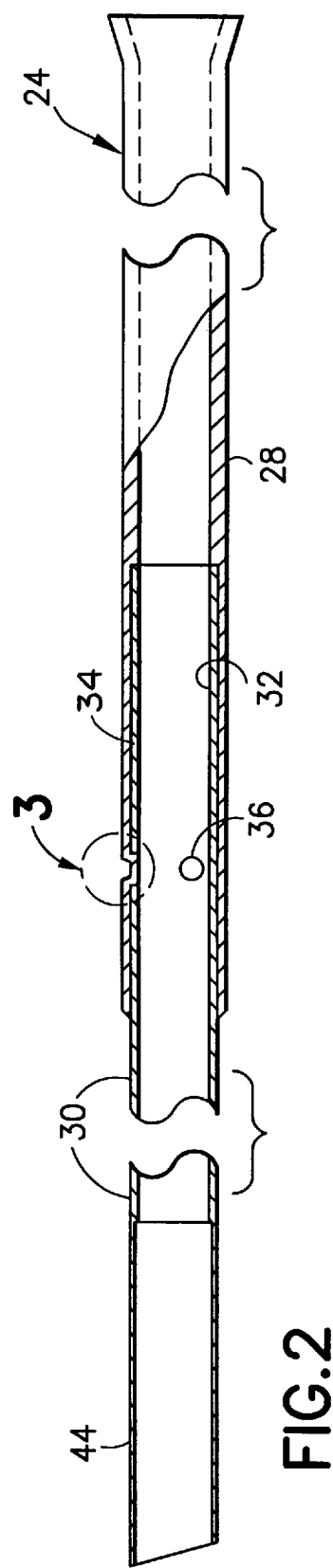
FIG. 2 is a partial cross-sectional view of a shaft used in the endoscope shown in FIG. 1.
Figure 3:
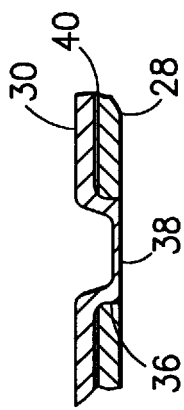
FIG. 3 is an enlarged view of area 3 shown in FIG. 2.

Referring also to FIGS. 2 and 3, the shaft frame 24 is shown. In this embodiment the frame 24 is a two-piece member comprising a first rear section 28 and a second front section 30. The rear section 28 is a substantially rigid or semi-rigid tube preferably made of metal, such as stainless steel. The rear tube section 28 may be considered semi-rigid because of its thin wall thickness and cantilevered connection to the housing 12. A protective outer sheath of elastomeric material may be provided around the frame 24. The rear section 28 extends about three-fourths the length of the shaft frame 24. The front interior of the rear section 28 has a seat 32. The front section 30 of the frame 24 comprises a tube made of malleable material. The rear end 34 of the front section 30 has holes 36 therethrough. The rear end 34 of the front section 30 is located in the front seat 32 of the rear section 28 and connected thereto. The front section 30 also has two different wall thicknesses. The wall at the rear end 34 of the front tube section 30 is thicker than wall at the front end 44. This provides the rear end 34 with sufficient thickness to prevent a tear or fracture to occur at the holes 36. In addition, the front end 44 is adapted to seat the distal tip with the fiber optic bundles and working channel.

As noted above, the connection of the front and rear sections comprises the rear or proximal end 34 of the front section 30 being located in the seat 32 inside the front or distal end of the rear section 28. The rear section 28 is deformed to form inwardly projecting sections or rivets 38 at the holes 36. The sections 38 project into the holes 36 and mechanically interlock the two tube sections 28, 30 together. The sections 38 are merely formed as inwardly extending dimples stamped into the rear section 28. Preferably, a suitable back support is located inside the two tube sections 28, 30 when the sections 38 are stamped to prevent piercing through the rear section 28 or otherwise excessively deforming the front of the rear section 28. In a preferred embodiment adhesive 40 is located at the joint between the two tube sections 28, 30 to assist in forming the fixed connection between the two tube sections. In alternate embodiments, additional and/or alternative means or methods could be used to fixedly connect the two tube sections to each other. For example, rather than through holes in the front section 30, the rear section could be formed into slots or grooves in the front section which do not extend entirely through the wall of the front section. The front section 30 could also be outwardly deformed into holes, slots or grooves of the rear section. The rear section could also coaxially extend into the front section. More than two tube sections could also be used.

Once the two tube sections 28, 30 are connected to each other, they form a unique shaft frame. The rear section 28, because it is semi-rigid or substantially rigid, provides the shaft 22 with sufficient rigidity to access a target area through an aperture in a patient that exerts force on the shaft. For example, the shaft can pass through a patient's urethra or pass through a surgical incision, such as used in laparoscopy. The front section 30 also has sufficient rigidity or column strength to be passed through the aperture in the patient without significantly deforming. However, because the front section is comprised of a malleable material, a user can shape or form the front section to a desired shape by hand before insertion into the aperture. The front section will substantially retain that shape. Thus, the user can bend the front section 30 to access a target area inside the patient that otherwise could be very difficult or impossible to access by a straight and wholly rigid/semi-rigid shaft. However, because the majority of the length of the shaft frame 24 is the straight substantially rigid/semi-rigid tube 28, the benefits and advantages of positioning control without deformation is provided along the majority of the length of the shaft. Thus, the shaft frame 24 is a hybrid frame having both structural rigidity along the rear section 28 and malleable reconfiguration shaping by hand at the distal end of the shaft. This provides overall shaft structural rigidity to relatively easily place the distal end 27 of the shaft in the general vicinity of the target area, and the precision, through reconfigurability by bending the front section 30, to angle the distal tip 26 directly at the target area.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An endoscope having an elongate shaft, the shaft comprising:

a first section along a majority of the length of the shaft, the first section having a semi-rigid tube; and a second section connected to a distal end of the first section, the second section having a malleable tube which is adapted to be formed to a desired shape by hand, wherein the first section provides the shaft with sufficient rigidity to access a target area through an aperture in a patient, that exerts force on the shaft, and the second section can be pre-formed before insertion of the shaft into the patient to have the desired shape when a distal end of the shaft reaches the target area.

2. An endoscope as in claim 1 wherein the malleable tube has a proximal end located inside the distal end of the semi-rigid tube.

3. An endoscope as in claim 2 wherein the malleable tube has holes in its proximal end.

4. An endoscope as in claim 3 wherein the semi-rigid tube is attached to the malleable tube at the holes.

5. An endoscope as in claim 4 wherein portions of the semi-rigid tube are deformed into the holes.

6. An endoscope as in claim 5 wherein the portions merely comprise inwardly extending dimples stamped into the semi-rigid tube.

7. An endoscope as in claim 1 wherein the malleable tube has at least two different wall thicknesses.

8. An endoscope having an elongate shaft, the shaft comprising:

a first semi-rigid tube; and a second tube connected to a distal end of the first tube, the second tube being comprised of a hand malleable material, wherein, at a connection area of the tubes to each other, at least one of the tubes has holes and the other tube has sections that project into the holes to attach the two tubes together.

9. An endoscope as in claim 8 wherein the first tube extends along a majority of the length of the shaft.

10. An endoscope as in claim 8 wherein the second tube has a proximal end located inside the distal end of the first tube.

11. An endoscope as in claim 10 wherein the first tube has a seat in its distal end for matingly receiving the proximal end of the second tube.

12. An endoscope as in claim 8 further comprising adhesive connecting the two tubes to each other.

13. An endoscope as in claim 8 wherein the second tube has the holes in its proximal end.

14. An endoscope as in claim 13 wherein portions of the first tube are deformed into the holes.

15. An endoscope as in claim 14 wherein the portions merely comprise inwardly extending dimples stamped into the first tube.

16. An endoscope as in claim 8 wherein the malleable tube has at least two different wall thicknesses.

17. A method of manufacturing an endoscope shaft comprising steps of:

providing a hand malleable tube with holes at a proximal end;

positioning a semi-rigid tube on the proximal end of the hand malleable tube over the holes; and deforming the semi-rigid tube to form sections that project into the holes of the hand malleable tube and thereby attach the two tubes to each other.

18. A method as in claim 17 further comprising attaching the two tubes to each other with adhesive.

19. A method as in claim 17 wherein the step of providing the hand malleable tube includes providing the hand malleable tube with two different wall thicknesses.

20. A method as in claim 17 wherein the step of deforming comprises stamping the semi-rigid tube to form inwardly extending dimples that project into the holes.

* * * * *